(12) United States Patent
Cool

(10) Patent No.: US 7,348,304 B1
(45) Date of Patent: Mar. 25, 2008

(54) FRAGRANCE MATERIAL

(76) Inventor: Laurence G. Cool, 2408 McKinley Ave., Berkeley, CA (US) 94703

( * ) Notice: Subject to any disclaimer, the term of this patent is extended or adjusted under 35 U.S.C. 154(b) by 675 days.

(21) Appl. No.: 10/905,175

(22) Filed: Dec. 20, 2004

(51) Int. Cl.
*C11B 9/00* (2006.01)
*C11D 3/50* (2006.01)
*A61Q 13/00* (2006.01)
*C07C 49/00* (2006.01)

(52) U.S. Cl. ............... 512/8; 512/15; 512/17; 512/18; 512/26; 568/300; 568/303; 568/338; 568/341; 568/343; 568/347

(58) Field of Classification Search ............ 512/8, 512/15, 17, 18, 26; 568/300, 303, 338, 341, 568/343, 347
See application file for complete search history.

(56) References Cited

U.S. PATENT DOCUMENTS

| 3,373,208 | A | 3/1968 | Blumenthal |
| 3,799,987 | A | 3/1974 | Kitchens et al. |
| 5,696,075 | A | 12/1997 | Chapuis et al. |
| 6,551,988 | B1 | 4/2003 | Munro |

OTHER PUBLICATIONS

F. Bohlmann et al, Phytochemistry, "Types of Sesquiterpenes from Artemisis Filifolia", vol. 22, No. 2, pp. 503-507, 1983, no month given.*

R. Ter Heide et al., in "Proc. 10th International Congress of Essential Oils, Flavors and Fragrances", Washington DC., Nov. 16-20, 1986, pp. 627-639 (1988).
F. Bohlmann et al., Phytochemistry, 22(2):503-507 (1983), no month given.
H. C. Brown et al., J. Am. Chem. Soc., 82(16):4233-4241, Aug. 20, 1960.
H. C. Brown et al., J. Am. Chem. Soc., 83(13):2951-2952, Jul. 5, 1961.

* cited by examiner

*Primary Examiner*—Brian Mruk

(57) ABSTRACT

The invention provides a novel fragrance material comprising a compound having the structure

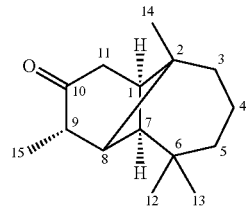

(IUPAC name (1R,2S,7R,8R,9S)-2,6,6,9-tetramethyltricyclo-[5.4.0.0$^{2,8}$]undecan-10-one). The novel fragrance material has a strong, pleasant cedar wood fragrance and is useful for imparting, strengthening, or improving the odor of perfumes and perfumed products. Methods for preparing the novel fragrance material are described.

13 Claims, No Drawings

FRAGRANCE MATERIAL

BACKGROUND OF THE INVENTION

This invention concerns a novel fragrance material, and perfumes and perfumed products comprising the novel material.

Cedar wood (heartwood of Eastern Red Cedar, i.e. *Juniperus virginiana*) has long been used as material for constructing or lining domestic storage spaces such as closets and chests. The wood is desirable for this purpose not only for its appearance but for its high content of an oil that consists primarily of a complex mixture of sesquiterpenoids. This oil gives cedar wood a characteristic and very pleasant fragrance, and it is also believed to act as a repellant to clothes moths. One problem with installed cedar wood is that its fragrance decreases markedly with time.

Cedarwood oil is produced commercially in large quantities by steam distillation of the heartwood of several members of the plant family Cupressaceae, particularly *Juniperus virginiana* and *Juniperus ashei* (in the U.S.A.), and of *Cupressus funebris* (in China). The oil is primarily used as a raw material in the fragrance industry, either in unmodified form or, more typically, after rectification and/or some chemical reaction to improve its fragrance characteristics. A solution of the oil, or modified forms thereof, is also marketed for temporarily restoring the fragrance of installed cedar wood.

The unmodified commercial oils, and rectified fractions thereof, have the disadvantage that they vary significantly in odor quality and character, depending on the source tree species and distillation and rectification methods used.

Another disadvantage of commercial cedarwood oils, and rectified fractions thereof, is that their odor impact is rather weak. This necessitates using fairly high percentages, typically around 10% or more, in perfume compositions to achieve a useful contribution to the fragrance. Furthermore, even at such concentrations, the cedar wood fragrance note is not very effectively imparted.

A further disadvantage of commercial cedarwood oils, and rectified fractions thereof, is that they may undergo undesirable chemical change during storage due to the action of light, moisture, and oxygen on carbon-carbon double bonds or susceptible functional groups of compounds in such oils or rectified fractions.

Previously-developed chemical treatments to enhance the fragrance utility of cedarwood oil, or rectified fractions thereof, include methylation, to produce mixtures rich in methyl cedryl ether (U.S. Pat. No. 3,373,208 to Blumenthal); acetylation, to produce mixtures rich in cedryl acetate or methyl cedryl ketone (U.S. Pat. No. 3,799,987 to Kitchens et al.); and oxidation, to produce mixtures rich in cedrene epoxide. These products, though useful fragrance materials, have odors that depart significantly from that of cedar wood. Thus the odor of methyl cedryl ether is characterized as "woody-amber"; that of methyl cedryl ketone as "musk-woody"; that of cedrene epoxide as "woody-amber-camphor"; that of cedryl acetate as "woody-vetiver".

Other synthetic fragrance compounds have odors with a cedarwood note but that likewise depart significantly from the odor of cedar wood itself. For example: (S)-alpha-ionone ("cedarwood, raspberry"); 1-(4,8-cyclododecadienyl)-1-propanone ("cedarwood, amber, pepper"—U.S. Pat. No. 6,551,988 to Munro); (−)-(1'R,2S)-2-methyl-4-(2',2',3'-trimethyl-3'-cyclopenten-1'-yl)-4-penten-1-ol ("sandalwood; cedar"—U.S. Pat. No. 5,696,075 to Chapuis and Blanc).

In the fragrance industry there is ongoing need to develop new fragrance materials to give perfumers and other persons in the art the ability to create new perfumes, air fresheners, candles, colognes, personal care products, etc. The particular fragrance character of cedar wood is considered very desirable.

Thus, there is need for new fragrance materials that more closely resemble the odor of cedar wood, that effectively impart their odor to perfume compositions at lower concentrations, and that are more stable, compared with existing fragrance materials.

BRIEF SUMMARY OF THE INVENTION

In one aspect the invention provides a novel fragrance material comprising the chemical compound (1R,2S,7R,8R,9S)-2,6,6,9-tetramethyltricyclo[5.4.0.0$^{2,8}$]undecan-10-one. For brevity and simplicity, this compound may also be referred to hereinafter as "the compound" or "the compound of the invention".

The compound of the invention possesses a strong, pleasant and characteristic cedar wood fragrance, and mixtures comprising the compound effectively impart this desirable fragrance note to perfumes and perfumed products.

In another aspect, the invention provides perfumes and perfumed products comprising the compound of the invention.

Accordingly, several advantages of the invention over existing, known fragrance materials are:

it provides a fragrance material that more effectively imparts the desirable odor of cedar wood;

it provides a fragrance material that is more potent, and is therefore effective at lower concentration in a perfume or perfumed product;

it provides a fragrance material that is stable.

Yet further advantages of the invention will be apparent from the following detailed description.

DETAILED DESCRIPTION OF THE INVENTION

The compound of the invention (IUPAC name (1R,2S,7R,8R,9S)-2,6,6,9-tetramethyltricyclo[5.4.0.0$^{2,8}$]undecan-10-one) has the structure

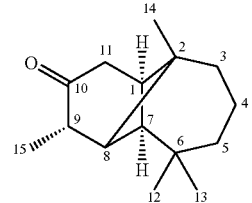

where carbon atoms numbered 1, 7 and 8 have R absolute stereochemistry and where carbon atoms numbered 2 and 9 have S absolute stereochemistry.

The compound has an intense, pleasant and characteristic cedar wood odor; it is diffusive and substantive; and it is also stable against the action of light, oxygen, and moisture. The odor properties of the compound are unobvious and surprising, as no prior knowledge would enable a practitioner of the art to predict these odor properties. Thus, a prior attempt to identify the compound or compounds responsible for the fragrance of cedar wood failed to disclose any such compound or compounds (R. ter Heide, J. Visser, L. M. van der Linde, and F. P. van Lier in *Flavors and Fragrances: A*

World Perspective, B. M. Lawrence, B. D. Mookherjee, and B. J. Willis (Eds.), Proceedings of the 10$^{th}$ International Congress on Essential Oils, Fragrances and Flavors, Washington D.C., 16-20 Nov. 1986, p. 627-639). Furthermore, no reports of the compound of the invention, whether synthetic or of natural occurrence, have been published. However, there is a previously-known, naturally-occurring compound (1R,2S,7R,8R,9R)-2,6,6,9-tetramethyltricyclo-[5.4.0.0$^{2,8}$] undecan-10-one ("the C-9 epimer" hereinafter) that is identical to the compound of the invention in all respects except for the stereochemistry at carbon atom 9 (F. Bohimann, C. Zdero, J. Jakupovic, H. Greger, Phytochemistry 22, 503-507 (1983)). The C-9 epimer possesses no distinctive or useful fragrance properties.

The odor properties of the compound of the invention make it a most suitable fragrance material, either in pure form or as the effective fragrant component in a natural or synthetic mixture. The phrases "novel fragrance material", "the material of the invention", or "the material" are used hereinafter to refer indiscriminately to any such mixture wherein (a) the compound is present at a concentration between about 0.1 and 100% by weight and (b) where the balance of the mixture consists of compounds that are present incidentally and that have little effect on the odor of the material other than as diluents. In reference to the material of the invention, "grade" is intended to mean a specific concentration by weight of the compound of the invention. "Fragrance material" is intended to mean a natural or artificial chemical substance or mixture that is useful as a component of a perfume. "Perfume" is intended to mean a mixture of two or more fragrance materials, if desired mixed with or dissolved in a suitable solvent, which is used to impart a desired odor to the skin, hair, or any consumer product for which an agreeable odor is indispensable or desirable. "Perfumed product" is intended to mean any consumer product into which one or more fragrance materials, or a perfume, are incorporated to impart an agreeable odor to the product.

The material of the invention may be used alone or in a perfume to impart, strengthen or improve the odor of a wide variety of perfumed products. Examples of such products are: fabric washing powders, washing liquids, fabric softeners and other fabric care products; detergents and household cleaning, scouring and disinfection products; air fresheners, room sprays and pomanders; soaps, bath and shower gels, shampoos, hair conditioners and other personal cleansing products; cosmetics such as creams, ointments, toilet waters, preshave, aftershave, body, skin and other lotions, talcum powders, body deodorants and antiperspirants, microporous perfumed slow release polymers, etc.

Known fragrance materials which can be advantageously combined with the material of the invention in a perfume are mentioned, for example, in S. Arctander, "Perfume and Flavor Chemicals" (Montclair, N.J., 1969); in S.

Arctander, "Perfume and Flavor Materials of Natural Origin" (Elizabeth, N.J., 1960); and in "Flavor and Fragrance Materials" (Allured Publishing Co., Carol Stream, Ill., 1997). Such known fragrance materials include natural products such as extracts, essential oils, absolutes, resinoids, resins, concretes etc.; and also synthetic materials such as hydrocarbons, alcohols, aldehydes, ketones, ethers, acids, esters, acetals, ketals, nitrites, etc., including saturated and unsaturated compounds, aliphatic, carbocyclic, and heterocyclic compounds.

Examples of known fragrance materials which can be used in combination with the material of the invention in a perfume are: geraniol, geranyl acetate, linalool, linalyl acetate, tetrahydrolinalool, citronellol, citronellyl acetate, dihydromyrcenol, dihydromyrcenyl acetate, tetrahydromyrcenol, terpineol, terpinyl acetate, nopol, nopyl acetate, 2-phenylethanol, 2-phenylethyl acetate, benzyl alcohol, benzyl acetate, benzyl salicylate, styrallyl acetate, benzyl benzoate, amyl salicylate, dimethylbenzylcarbinol, trichloromethylphenylcarbinyl acetate, p-tert-butylcyclohexyl acetate, isononyl acetate, vetiveryl acetate, vetiverol, α-hexylcinnamaldehyde, 2-methyl-3-(p-tert-butylphenyl)propanal, 2-methyl-3-(p-isopropylphenyl)propanal, 2-(p-tert-butylphenyl)-propanal, 2,4-dimethyl-cyclohex-3-enyl-carboxaldehyde, tricyclodecenyl acetate, tricyclodecenyl propionate, 4-(4-hydroxy-4-methylpentyl)-3-cyclohexenecarboxaldehyde, 4-(4-methyl-3-pentenyl)-3-cyclohexenecarboxaldehyde, 4-acetoxy-3-pentyl-tetrahydropyran, 3-carboxymethyl-2-pentylcyclopentane, 2-n-heptylcyclopentanone, 3-methyl-2-pentyl-2-cyclopentenone, n-decanal, n-dodecanal, 9-decen-1-ol, phenoxyethyl isobutyrate, phenylacetaldehyde dimethyl acetal, phenylacetaldehyde diethyl acetal, geranyl nitrile, citronellyl nitrile, cedryl acetate, 3-isocamphylcyclohexanol, cedryl methyl ether, cedrene epoxide, isolongifolanone, aubepine nitrile, aubepine, heliotropin, coumarin, eugenol, vanillin, diphenyl oxide, hydroxycitronellal, ionones, methylionones, isomethylionones, irones, cis-3-hexenol and esters thereof, indan musks, tetralin musks, isochroman musks, macrocyclic ketones, macrolactone musks, ethylene brassylate, etc.

Solvents which can be used for perfumes that comprise the material of the invention are, for example: ethanol, isopropanol, diethyleneglycol monoethyl ether, dipropylene glycol, diethyl phthalate, triethyl citrate, isopropyl myristate, etc.

In addition to the material of the invention, other agents can be used in conjunction with the perfume. Well-known agents such as surfactants, emulsifiers, and polymers to encapsulate the fragrance can also be employed without departing from the scope of the present invention. Furthermore, perfumes comprising the material of the invention can be adsorbed on a carrier which serves both to distribute the fragrances finely within the product and to release them in a controlled manner during use. Such carriers can be porous inorganic materials such as light sulphate, silica gels, zeolites, gypsums, clays, clay granules, etc., or organic materials such as woods and cellulose-based substances.

Other known fragrance materials, solvents, agents, and carriers suitable for combining with the material of the invention in perfumes or perfumed products will be apparent to a practitioner in the art and can be employed without departing from the scope of the present invention.

The amount of the material of the invention to be used in a perfume or perfumed product depends on the grade of the material selected and the target level of the compound of the invention in the perfume or product. The target level at which the compound can be advantageously provided in perfume compositions or in perfumed products may vary within wide limits and depends, inter alia, on the nature of the product, the nature and the quantity of the other components of the perfume in which the material is used, and the olfactive effect desired. It is therefore only possible to specify wide limits, which, however, provide sufficient information for the specialist in the art to be able to use the material of the invention for his/her specific purpose.

In perfumes an amount of at least 0.02% by weight of the compound of the invention will generally have a clearly perceptible olfactive effect. For fragrance-rounding effects, my preferred range is from 0.05 to about 0.2% by weight of the compound based on the total. For imparting a more pronounced cedar wood fragrance, higher levels may be used, preferably at least 0.2% by weight, most preferably between about 0.5 and about 20% by weight of the total. However, these values are not intended to represent limits because the experienced perfumer may still obtain useful effects with lower concentrations or can formulate new fragrance compositions with even higher concentrations.

In a perfumed product, an amount of at least 2 parts per million (ppm) by weight of the compound will generally have a perceptible olfactive effect. More preferably the amount is at least 5 ppm by weight, most preferably at least 25 ppm by weight.

The only upper limits on the amount of the material of the invention in perfumes and perfumed products are those dictated by considerations common to the art, such as cost, the olfactive effect desired, amounts of other components required, the nature of the end product, etc.

The material of the invention may be prepared by isolation from a natural source such as heartwood of species of the plant family Cupressaceae. In particular, *Juniperus chinensis* var. *torulosa* and var. *variegate* are suitable sources, since the heartwood of each comprises, by weight, about 0.5 ppm of the compound of the invention and about 4.5 ppm of the C-9 epimer. Other species of *Juniperus* or *Cupressus* with very fragrant heartwood are likely to be equally suitable sources of the material of the invention and may be so employed without departing from the scope of the invention.

Appropriate methods of distillation and fractionation and/or rectification to isolate the material of the invention will be apparent to a specialist in the art. My preferred method for isolation of the material from a natural heartwood source entails:

(1) solvent extraction of a crude oil from the ground wood;

(2) hydrodistillation of the crude oil over a slightly alkaline brine to give an essential oil;

(3) repeated preparative low-pressure (and optional high-pressure) liquid chromatographic fractionation of the essential oil, using silica gel adsorbents and step gradients of ethyl acetate in hexane as eluents; and (4) optional preparative gas chromatography to enhance enrichment of the compound of the invention in selected fractions.

The purpose of using an alkaline brine in step (2) is to (a) avoid acid-catalyzed decomposition or alteration of labile oil components, and (b) increase the ratio of the compound of the invention to the C-9 epimer through keto-enol tautomerization.

For cost reasons, the chromatographic isolation process is preferably terminated at some intermediate stage, typically when the compound of the invention is enriched to a level of at least about 0.1% by weight, more preferably at least 1% by weight, whereby a fragrant fraction comprising the compound of the invention is provided. Such a fragrant fraction itself provides a useful grade of the material of the invention that can be incorporated in a perfumed product or admixed with known fragrance materials in a perfume.

The material of the invention may also be prepared by subjecting the C-9 epimer to keto-enol tautomerization using dilute acid or, more preferably, dilute base as catalyst. The isomerization reaction yields a mixture of the two epimers wherein, surprisingly, the compound of the invention predominates over the C-9 epimer in a ratio of about 6:1 at equilibrium.

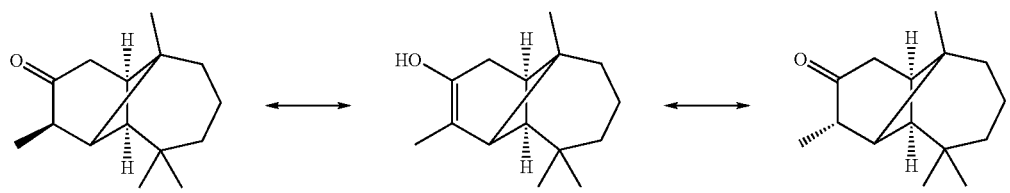

Suitable conditions for effecting the isomerization, including choice and concentration of catalyst and selection of the reaction temperature, will be apparent to a practitioner in the art. My preferred method for this reaction uses dilute aqueous sodium hydroxide at about 0.0001 N and a temperature of about 100° C. Under these conditions, the isomerization reaction may be terminated after 3 hours, preferably after 8 hours, most preferably after 24 hours, to give a mixture containing from about 60 to about 85% by weight of the compound of the invention, the balance being the C-9 epimer. Such a mixture provides a useful grade of the material of the invention that can be incorporated in a perfumed product or admixed with known fragrance materials in a perfume.

My most preferred method for preparing the material of the invention is by synthesis from an unsaturated hydrocarbon by hydroboration followed by chromic acid oxidation using well-known techniques (H. C. Brown, K. J. Murray, L. J. Murray, J. A. Snover, G. Zweifel, JACS 82, 4233-4241 (1960); H. C. Brown, C. P. Garg, JACS 83, 2951-2952 (1961)). In particular, α-longipinene is reacted with diborane, the latter being conveniently generated in the reaction mixture from an alkali metal borohydride and a Lewis acid. The resulting borohydride adduct is subsequently oxidized with chromic acid to give the ketonic product. Surprisingly, the product consists solely of the desired isomer, with none of the C-9 epimer being formed. Racemic synthetic α-longipinene (prepared, for example, according to M. Miyashita and A. Yoshikoshi, JACS 96, 1917-1925 (1974)) may be used as the starting material to give an approximately 50:50 mixture of the compound of the invention and its enantiomer in high yield, wherein the enantiomer is expected to have little effect on the odor of the product other than diluting it. Most preferably, enantiomerically pure (+)-α-longipinene (IUPAC name (1R,2S,7R,8R)-2,6,6,9-tetramethyltricyclo[5.4.0.0$^{2,8}$]undec-9-ene) is used as the starting material, giving the compound of the invention in high yield and purity.

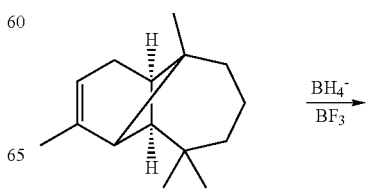

-continued

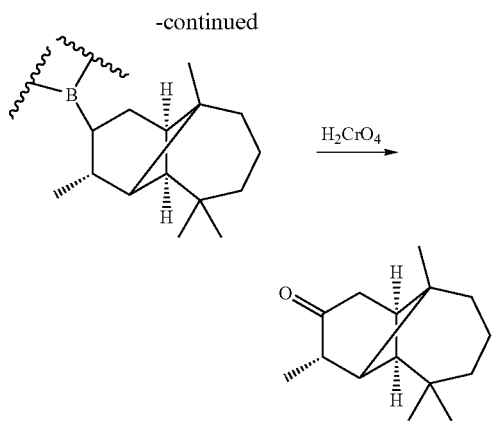

The following Examples are intended to illustrate the invention without limiting it in any way. The abbreviations in the examples have their usual meaning in the art.

Analytical instrumentation used in the following examples is a follows:

Gas chromatography (GC): dual WCOT columns (5% phenyl and 50% phenyl methylpolysiloxane stationary phases) and dual flame ionization detectors at 280° C. Injector temperature 250° C., columns programmed from 90° C. to 250° C. at 6° C. per minute.

GC-mass spectroscopy (GC-MS): 5% phenyl methylpolysiloxane stationary phase; injector and column temperatures as above; EIMS detection at 70 eV. Selected ion monitoring at m/z 124 was used to sensitively detect the compound of the invention in fractions from conventional (LC) and high-performance (HPLC) liquid chromatography.

Enantioselective GC: WCOT column (10% permethyl-β-cyclodextrin in OV-1701 stationary phase) with flame ionization detector at 250° C. Injector temperature 225° C., column programmed from 90° C. to 150° C. at 1° C. per minute.

NMR: Bruker AV-500, 5 mm broad-band Z-gradient probe.

EXAMPLE I

Enrichment and Isolation of the Compound of the Invention and the C-9 Epimer from *Juniperus chinensis* var. *torulosa* Heartwood In 1.3-kg batches, chipped and ground *Juniperus chinensis* var. *torulosa* heartwood (9 kg total) was extracted by covering the wood with n-hexane for 24 hrs in a large glass column, draining off the solution, and then repeating the extraction a second time. The total yield of crude oil was 515 g after solvent removal. The crude oil was hydrodistilled in 103-g batches for three days from 800 ml of an aqueous solution of 240 g sodium chloride and 10 g of sodium bicarbonate, with 20 ml of n-hexane in the receiver and continuous return of condensed water to the distillation flask. A total yield of 450 g of pale yellow oil was obtained after solvent removal.

This hydrodistilled oil was separated by normal-phase LC of 30-g batches, using these conditions: 1200 g silica gel adsorbent (−200 mesh); eluent step gradients of increasing percentages of ethyl acetate in n-hexane (1500 ml 7%, 1000 ml 26%, 1000 ml 50%), followed by decreasing ethyl acetate concentrations (250 ml 20%, 550 ml 7%). Five fractions of the following volumes were collected: Fraction 1 (500 ml), Fraction 2 (500 ml), Fraction 3 (900 ml), Fraction 4 (620 ml), Fraction 5 (1780 ml).

Fraction 3 (30 g total after solvent removal) had an enhanced cedar wood fragrance compared with the original oil, and it was shown by GC-MS to contain the compound of the invention and the C-9 epimer in comparable amounts (about 0.1% each). The balance of this fragrant fraction consisted of numerous compounds that were present in the original oil, but which do not contribute to the fragrance of the fraction to a significant degree. This fragrant fraction 3 itself provides a useful grade of the material of the invention that can be incorporated in a perfumed product or admixed with known fragrance materials in a perfume.

LC fraction 3 was further separated by normal-phase LC of five 6-g batches using these conditions: 200 g silica gel adsorbent (60 micron particle size); 12 psig nitrogen pressure; eluent step gradients of increasing percentages of ethyl acetate in n-hexane (300 ml 3%, 300 ml 5%, 150 ml 16%, 150 ml 26%), followed by decreasing ethyl acetate concentrations (100 ml 10%, 130 ml 3%). Six fractions of the following volumes were collected: Fraction 3-1 (350 ml), Fraction 3-2 (150 ml), Fraction 3-3A (70 ml), Fraction 3-3B (100 ml), Fraction 3-3C (100 ml), Fraction 3-4 (360 ml).

Fraction 3-3B (about 1 g total after solvent removal) had a markedly enhanced cedar wood fragrance, and was shown by GC-MS to contain the compound of the invention and the C-9 epimer in comparable amounts (about 2% each). The balance of this fragrant fraction consisted of numerous compounds that were present in the original oil, but which do not contribute to the fragrance of the fraction to a significant degree. This fragrant fraction 3-3B itself provides a useful grade of the material of the invention that can be incorporated in a perfumed product or admixed with known fragrance materials in a perfume.

Fraction 3-3B was further separated 7 mg at a time by isocratic normal phase semi-preparative HPLC under these conditions: silica gel adsorbent (5 micron particle size, column dimensions 10 mm i.d.×250 mm), eluent 5% ethyl acetate in n-hexane, flow rate 4 ml per min, RI detection. Ten fractions were collected, one of which (Fraction 3-3B-5, 110 mg) was highly fragrant and was very rich in the compound of the invention and the C-9 epimer (about 20% each). The balance of this fragrant fraction consisted of numerous compounds that were present in the original oil, but which do not contribute to the fragrance of the fraction to a significant degree. This fragrant fraction 3-3B-5 itself provides a useful grade of the material of the invention that can be incorporated in a perfumed product or admixed with known fragrance materials in a perfume.

Fraction 3-3B-5 was subjected to preparative GC (4 mm i.d. packed column, SE-30 stationary phase, 210° C. column temperature, 225° C. injector temperature, helium carrier gas, TC detector at 225° C.) with repeated 1.5 mg injections, yielding about 40 mg of a fraction that consisted of a mixture of about 50% each of the compound of the invention and the C-9 epimer essentially free of all other compounds. This mixture itself provides a useful grade of the material of the invention that can be incorporated in a perfumed product or admixed with known fragrance materials in a perfume.

The compound of the invention and the C-9 epimer were each purified to over 98% by repeated semi-preparative HPLC separations of 0.5 mg portions of the mixture from preparative GC using the same HPLC apparatus as above but with 3% ethyl acetate eluent at a flow rate of 3 ml per min. The yield after solvent removal was about 15 mg each of the compound of the invention and the C-9 epimer. The purified compound of the invention provides a useful grade of the material of the invention that can be incorporated in a perfumed product or admixed with known fragrance materials in a perfume.

Analytical data for the compound of the invention are:

GC-mass spectroscopy, 70 eV, m/z (% rel. int.): 220 (8) [M]$^+$, 205 (1), 177 (20), 163 (13), 149 (21), 137 (18), 124 (100), 109 (75), 95 (64), 82 (57), 81 (66), 67 (39), 55 (37), 41 (48).

$^{13}$C NMR (125.77 MHz, $C_6D_6$, solvent ref. 128.0, ppm from TMS): 213.4 (s), 56.9 (d), 48.3 (d), 46.8 (t), 43.1 (d), 41.3 (s), 41.0 (t), 39.6 (t), 36.8 (d), 32.4 (s), 28.0 (q), 27.5 (q), 21.7 (t), 21.3 (q), 15.4 (q).

$^1$H NMR (500.13 MHz, $C_6D_6$, solvent ref. 7.15, ppm from TMS): 2.48 (dd, J=19, 1 Hz; 1H), 2.45 (qd, J=7, 1 Hz; 1H), 2.22 (ddd, 19, 3, 1 Hz; 1H), 1.72 (dt, 7, 3 Hz; 1H), 1.50 (dd, 7, 2 Hz; 1H), 1.40 (m; 2H), 1.33 (m; 2H), 1.22 (m; 2H), 1.08 (d, J=7 Hz; 3H), 0.95 (s; 1H), 0.76 (s; 3H), 0.74 (s; 3H), 0.57 (s; 3H).

EXAMPLE II

Preparation of the Material of the Invention by Subjecting (1R,2S,7R,8R,9R)-2,6,6,9-tetramethyltricyclo[5.4.0.0$^{2,8}$]undecan-10-one to Keto-Enol Tautomerization 1 mg of (1R,2S,7R,8R,9R)-2,6,6,9-tetramethyltricyclo-[5.4.0.0$^{2,8}$]-undecan-10-one (i.e. the C-9 epimer of Example I) was dissolved in 0.8 ml of ethanol and the solution divided equally into four screw cap vials. To each vial was added 0.75 ml of 10$^{-4}$ M aqueous potassium hydroxide, after which the capped vials were placed in a 100° C. oven. After selected intervals, a vial was withdrawn and the solution extracted twice with n-hexane. The hexane extracts were analyzed by dual-column GC and enantioselective GC, giving the following percentages of Reactant and Product, the latter being the compound of the invention.

| Time (hr) | Reactant (%) | Product (%) |
|---|---|---|
| 0 | 100 | 0 |
| 1 | 82 | 12 |
| 3 | 41 | 59 |
| 18 | 17 | 83 |
| 42 | 14 | 86 |

The isomerization reaction thus provides useful grades of the material of the invention comprising the compound of the invention at concentrations up to about 86% by weight, depending on reaction time.

EXAMPLE III

Preparation of the Compound of the Invention from (+)-alpha-longipinene

All reactions were carried out at 25° C. In a sealed septum vial, 225 mg of (+)-α-longipinene (IUPAC name (1R,2S, 7R,8R)-2,6,6,9-tetramethyltricyclo[5.4.0.0$^{2,8}$]undec-9-ene) were added to a solution of 30 mg of lithium borohydride in 0.8 ml dry ethyl ether. A solution of 40 microliters of boron trifluoride etherate in 120 microliters of dry ethyl ether was injected through the septum over the course of 15 minutes. After a further 2 hours, excess borohydride was destroyed by addition of 0.15 ml of water.

A solution of 0.26 g of potassium dichromate and 0.37 g of sulfuric acid in 1.1 ml water was added to the reaction mixture over the course of 15 minutes. After holding for 90 minutes with occasional shaking, the upper ether layer was withdrawn and the aqueous layer extracted several times with 0.5 ml ethyl ether. The combined ether extracts were washed with aqueous sodium bicarbonate, then with water, dried over anhydrous sodium sulfate, and the solvent removed by evaporation.

Product yield, based on amount of the compound of the invention, was 82% of theoretical. As determined by GC and enantioselective GC, the product comprised more than 90% by weight of the compound of the invention, with none of the C-9 epimer detected.

The odor character of the product is described as: "Cedar, woody, cigar box, tobacco, slightly animal—civet. Long-lasting in dry-down."

Thus the synthetic product provides a useful grade of the material of the invention that can be incorporated in a perfumed product or admixed with known fragrance materials in a perfume.

EXAMPLE IV

Determination of Approximate Aqueous Odor Threshold of the Compound of the Invention 2 mg of the compound of the invention according to Example I were dissolved in 1.0 ml ethanol and serial dilutions made in deionized water to give test solutions of the compound at concentrations of 100, 20, 4, and 1 ppb.

Pairs of loosely-covered beakers were presented to three subjects, one beaker containing deionized water and the other a test solution. The subjects were asked to identify the beaker containing the test solution by removing the covers and sniffing, with the following results ("X" means correct positive identification, "-" means unable to identify):

| Compound concentration (ppb) | Subject 1 | Subject 2 | Subject 3 |
|---|---|---|---|
| 100 | X | X | X |
| 20 | X | — | X |
| 4 | X | — | X |
| 1 | — | — | X |

EXAMPLE V

Assessment of Stability of the Compound of the Invention 50 ml of a 250-ppb aqueous solution of the compound of the invention according to Example I was held in a covered 100 ml glass weighing bottle for seven months. Environmental conditions were ambient room light (fluorescent and indirect sunlight during daytime; dark at night) and temperature (16-26° C.). The bottle was opened approximately bi-weekly, admitting fresh air and allowing olfactory assessment of the odor strength. No decrease in odor intensity was evident after seven months.

EXAMPLE VI

Cedar Perfume Formulations

| Ingredients | VI(A) Parts by weight | VI(B) Parts by weight | VI(C) Parts by weight |
|---|---|---|---|
| Bergamot Argentina | 75 | 75 | 75 |
| Bois de Rose | 100 | 100 | 100 |
| Cedarwood oil Texas | 100 | 100 | 100 |
| Chamomile oil Roman | 20 | 20 | 20 |
| Lavandin grosso | 100 | 100 | 100 |
| Lavender 40/42 Bulgarian | 70 | 70 | 70 |
| Spruce oil | 25 | 25 | 25 |
| Material of the invention according to Example III | — | 2 | 0.5 |
| Dipropylene glycol | 510 | 508 | 509.5 |
| TOTAL | 1000 | 1000 | 1000 |

The olfactive effect of the compound of the invention in formulations VI(B) and VI(C), compared to formulation VI(A), is summarized: "Blends in well, enhances the cedar character of the fragrance, rounds the fragrance and pulls it together."

EXAMPLE VII

Lavender Perfume Formulations

| Ingredients | VII(A) Parts by weight | VII(B) Parts by weight | VII(C) Parts by weight |
|---|---|---|---|
| Clove stem Madagascar | 30 | 30 | 30 |
| Rose oxide | 10 | 10 | 10 |
| Geranium Chinese | 120 | 120 | 120 |
| Juniper berry | 20 | 20 | 20 |
| Lavender 40/42 Bulgarian | 300 | 300 | 300 |
| Patchouli oil light | 50 | 50 | 50 |
| Sandela | 10 | 10 | 10 |
| Ylang II | 80 | 80 | 80 |
| Material of the invention according to Example III | — | 2 | 0.5 |
| Dipropylene glycol | 380 | 378 | 379.5 |
| TOTAL | 1000 | 1000 | 1000 |

The olfactive effect of the compound of the invention in formulations VII(B) and VII(C), compared to formulation VII(A), is summarized: "Blends in well, enhances the character of the fragrance, rounds the fragrance and pulls it together."

What is claimed is:

1. A fragrance material comprising an amount between about 0.1 and 100% by weight of a compound having the structure

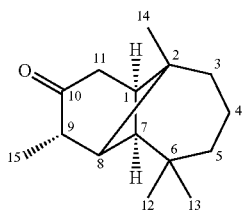

where carbon atoms numbered 1, 7 and 8 have R absolute stereochemistry and where carbon atoms numbered 2 and 9 have S absolute stereochemistry.

2. A method of preparing the fragrance material according to claim 1, comprising
   (a) hydroborating (1R,2S,7R,8R)-2,6,6,9-tetramethyltricyclo[5.4.0.0$^{2,8}$]undec-9-ene, followed by
   (b) oxidizing the product of step (a).

3. A method of preparing the fragrance material according to claim 1, comprising subjecting (1R,2S,7R,8R,9R)-2,6,6,9-tetramethyltricyclo-[5.4.0.0$^{2,8}$]undecan-10-one to keto-enol tautomerization.

4. The fragrance material of claim 1, wherein the amount of said compound in said fragrance material is at least 1% by weight.

5. A method of preparing the fragrance material according to claim 4, comprising
   (a) hydroborating (1R,2S,7R,8R)-2,6,6,9-tetramethyltricyclo[5.4.0.0$^{2,8}$]undec-9-ene, followed by
   (b) oxidizing the product of step (a).

6. A method of preparing the fragrance material according to claim 4, comprising subjecting (1R,2S,7R,8R,9R)-2,6,6,9-tetramethyltricyclo-[5.4.0.0$^{2,8}$]undecan-10-one to keto-enol tautomerization.

7. A perfume comprising an amount of at least 0.02% by weight of a compound having the structure

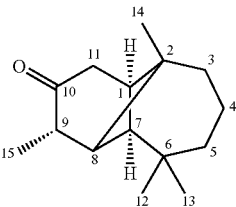

where carbon atoms numbered 1, 7 and 8 have R absolute stereochemistry and where carbon atoms numbered 2 and 9 have S absolute stereochemistry.

8. The perfume of claim 7, wherein the amount of said compound in said perfume is at least 0.05% by weight.

9. The perfume of claim 8, wherein the amount of said compound in said perfume is at least 0.2% by weight.

10. The perfume of claim 9, wherein the amount of said compound in said perfume is between about 0.5 and about 20% by weight.

11. A perfumed product comprising an amount of at least 2 parts per million by weight of a compound having the structure

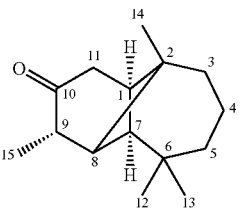

where carbon atoms numbered 1, 7 and 8 have R absolute stereochemistry and where carbon atoms numbered 2 and 9 have S absolute stereochemistry.

12. The perfumed product of claim 11, wherein the amount of said compound in said perfumed product is at least 5 parts per million by weight.

13. The perfumed product of claim 12, wherein the amount of said compound in said perfumed product is at least 25 parts per million by weight.

* * * * *